United States Patent [19]

Getman et al.

[11] Patent Number: 4,801,665
[45] Date of Patent: Jan. 31, 1989

[54] RESIN METHOD FOR MAKING SULFOXIDE FOR SOLID PHASE PEPTIDE SYNTHESIS

[75] Inventors: Daniel P. Getman, St. Louis; Robert M. Heintz, Ballwin, both of Mo.

[73] Assignee: Monsanto Company, St. Louis, Mo.

[21] Appl. No.: 947,651

[22] Filed: Dec. 30, 1986

[51] Int. Cl.$^4$ ............................ C08F 8/34; C08F 8/06
[52] U.S. Cl. ................................. 525/350; 525/359.4; 525/387
[58] Field of Search ............... 525/350, 383, 387, 388, 525/359.4, 54.1, 54.11

[56] References Cited

U.S. PATENT DOCUMENTS 3,995,094 11/1976 Crosby ............................ 525/333.4

Primary Examiner—Christopher Henderson
Attorney, Agent, or Firm—Linda L. Lewis; James W. Williams, Jr.; Arnold H. Cole

[57] ABSTRACT

A resin for solid phase peptide synthesis and a method for synthesizing the resin wherein the resin has a sulfoxide linkage which is stable to strong acid deprotecting conditions. The linkage can be reduced to a sulfide linkage which allows cleavage of the peptide from the resin under mild acid conditions.

4 Claims, No Drawings

RESIN METHOD FOR MAKING SULFOXIDE FOR SOLID PHASE PEPTIDE SYNTHESIS

FIELD OF THE INVENTION

The invention relates to a resin support for solid phase peptide synthesis and a method of synthesizing the resin support.

DESCRIPTION OF RELATED ART

The synthesis of peptides is generally carried out through the condensation (or coupling) of the carboxyl group of an amino acid, and the amino group of another amino acid, to form a peptide bond. A sequence can be constructed by repeating the condensation of individual amino acids in stepwise elongation, or, in some cases, by condensation between two preformed peptide fragments (fragment condensation). In both types of condensations, the amino and carboxyl groups that are not to participate in the reaction must be blocked (or protected) with protecting groups. In addition, reactive side chain functionalities of the amino acids also need to be protected.

A successful synthesis of a large peptide by a series of condensation reactions must achieve nearly quantitative recoveries for each chemical step. This requirement has been met by solid-phase peptide synthesis, pioneered by R. B. Merrifield. In such a synthesis, the peptide chain is normally attached by a benzyl-type carboxyl-protecting group to an insoluble polystyrene resin. A first amino acid is attached to the resin through a benzylic ester linkage, is deprotected at its amino site, and coupled with a second amino acid carrying a protected α-amino group, to produce a protected dipeptide ester. The protecting group is removed with trifluoroacetic acid, neutralized to form the free amine with base, and coupled to a second N-protected amino acid. After many repetitions of these steps, the complete peptide is cleaved from the resin with acid treatment. By using the insoluble resin support it is possible to isolate the product of each coupling reaction by filtering the resin and washing it free of by-products and excess starting materials. Barany, G. and Merrifield, R. B., "The Peptides, Vol. 2", Academic Press, Inc., New York, 1979, pp. 1-284; and Kemp-Vellaccio, "Organic Chemistry", pp. 1030-1032 (1980).

In solid phase peptide synthesis, the peptide-resin link is critical to the synthesis procedure. The link must be stable to the deprotection of the amino blocking groups, which typically entails the use of concentrated acid. If the linkage is not stable to deprotecting conditions, the peptide will be prematurely cleaved from the resin. Additionally, the linkage must be readily cleaved upon completion of the synthesis of the peptide, preferably under conditions that will not damage the eptide being recovered.

A number of approaches have been taken to improve the peptide-resin linkage. Merrifield developed a phenylacetamidomethyl linkage which is more stable to the strong acid conditions required to deprotect the amino groups. (Stewart, J. M. and Young, J. D., *Solid Phase Peptide Synthesis*, second edition, Pierce Chemical Co., Rockford, Illinois, pp. 11 and 12 and Gross, E. and Meienhofer, J., *The Peptides, Analysis, Synthesis, Biology*, Vol. 2, Academic Press, 1980, pp 3-250).

Because, as peptides become larger and more complex, they are less stable to the acidic condition necessary to deprotect and cleave, researchers developed a peptide resin link that can be cleaved by milder reagents. Wang developed a p-alkoxybenzyl alcohol resin that can be cleaved by 25% trifluoroacetic acid in dichloromethane. Stewart, Id. at 12, 13.

In an attempt to find milder conditions for cleavage, Tam, (U.S. Pat. No. 4,507,230) developed a method of reducing the acidity function of the strong acid used in cleavage, typically anhydrous hydrogen fluoride, by the use of a suitable weak base which would remain largely unprotonated and nucleophilic under the resulting acidic conditions.

None of the above references has disclosed a peptide-resin linkage for solid phase peptide synthesis which affords the combination of acid stability as well as ready cleavage under mild acid conditions.

J. M. Samanen and E. Bradelis disclose in their paper "The p-Methylsulfinylbenzyl Group, A Selectively Cleavable Carboxyl Protecting Group," 9th American Peptide Symposium in Toronto, June 23-28, 1985, a p-methylsulfinylbenzyl group which is useful as a carboxyl protecting group to be used in solution phase peptide synthesis. The sulfoxide substituted benzylic ester linkage is stable to the trifluoroacetic acid conditions used to deprotect the amino groups. When the sulfoxide is reduced to a sulfide, the ester group is "unlocked" and is cleavable in anhydrous trifluoroacetic acid. This protecting group has not been disclosed for use in solid phase peptide synthesis.

We have discovered a resin for solid phase peptide synthesis that provides both stability to strong acid conditions and ready cleavage under relatively mild acid conditions to provide a peptide and a resin.

SUMMARY OF THE INVENTION

The Resin

The present invention involves a resin for solid phase peptide synthesis and a method for synthesizing the resin. The resin comprises the structure

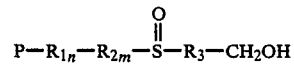

where P is the polymer support, $R_1$ is a substituted or unsubstituted aromatic, $R_2$ is an alkyl having from 1 to 20 carbons, $R_3$ is a substituted or unsubstituted phenyl and n and m independently equal 1 or 0.

The Resin Synthesis

The method of synthesizing a resin for solid phase peptide synthesis comprises (1) reacting a polymer support, P, capable of undergoing a nucleophilic reaction with a mercaptan of the formula

where $R_3$ is a substituted or unsubstituted phenyl, to form a sulfide resin of the formula

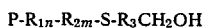

where $R_1$ is a substituted or unsubstituted aromatic, $R_2$ is an alkyl having 1 to 20 carbon atoms and n and m independently equal 1 or 0 and (2) oxidizing the sulfide resin to form a sulfoxide resin of the formula

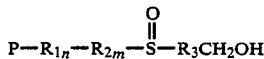

where $R_1$, $R_2$, $R_3$, n and m are defined above.

DETAILED DESCRIPTION OF THE INVENTION

The Resin

The resin of the present invention has the structure

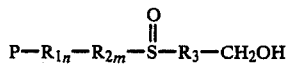

where P is the polymer support, $R_1$ is a substituted or unsubstituted aromatic, preferably an unsubstituted phenyl, and $R_2$ is an alkyl having 1 to 20 carbon atoms, preferably methylene. $R_3$ is a substituted or unsubstituted phenyl, preferably an unsubstituted phenyl, and n and m independently equal 1 or 0. If $R_1$ and $R_3$ are substituted, the substituents should be such that they will not react under the peptide synthesis conditions. Examples of suitable substituents for $R_1$ and $R_3$ are alkyls such as methyl or ethyl, aryls such as phenyl, alkenes such as propene, alkynes such as hexyne, nitro groups and halogens such as chloro, fluoro or bromo groups.

The polymer support can be any of a number of polymers, copolymers or combinations of polymers such as polyamide, polysulfamide, substituted polyethylenes, polyethyleneglycol, phenolic resins, polysacharides, or polystyrene. The polymer support must be insoluble and inert to the solvents used in peptide synthesis. Preferably, the support should be of a size and shape that allow easy handling and filtration from liquids. Preferably, the solvent should swell in the solvents used for synthesis to allow all reagents to penetrate throughout the polymer particle, allowing access to all reaction sites within the polymer particle. The preferred polymer support is a gel prepared by suspension copolymerization of styrene and about one percent of m-divinylbenzene or crosslinking agent. Such crosslinked gels swell in organic solvents to about 5 to 6 times their dry volume. The swelling allows solvents and reactants access to the reaction sites on the polymer and allows reaction in the interior of the polymer as well as the exterior surface.

Functional groups can be introduced to this polymer by chloromethylation which can be accomplished by using chloromethylmethylether. The chloromethylated crosslinked polystyrene gel is referred to in the art as the Merrifield resin. The Merrifield resin is described in further detail in Stewart, J.M. and Young, J.D., *Solid Phase Peptide Synthesis*, second edition, Pierce Chemical Co., Rockford, Illinois which is hereby incorporated by reference.

The preferred resin is of the formula

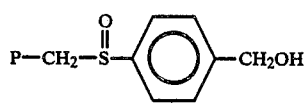

where P is crosslinked polystyrene resin.

The resin is used for solid phase peptide synthesis which is described in detail in copending patent application Ser. No. 946,558 which is hereby incorporated by reference.

The Resin Synthesis

The resin is synthesized by reacting a polymer support, P, capable of undergoing a nucleophilic reaction with a mercaptan of the formula $HSR_3CH_2OH$ where $R_3$ is a substituted or unsubstituted phenyl, to form a sulfide resin and oxidizing the sulfide resin to form a sulfoxide resin.

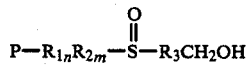

where $R_1$ is a substituted or unsubstituted aromatic, $R_2$ is an alkyl having 1 to 20 carbon atoms, $R_3$ is a substituted or unsubstituted phenyl and n and m independently equal 1 or 0.

The mercaptan is of the formula $HS-R_3CH_2OH$ where $R_3$ is a substituted or unsubstituted phenyl. Examples of the sulfide compound are p-(mercapto) benzyl alcohol, o-(mercapto)benzyl alcohol, p-(mercapto)o-methylbenzyl alcohol, or p-(mercapto)o-chlorobenzyl alcohol. The preferred mercaptan is p-(mercapto)benzyl alcohol. The reaction takes place in the presence of a tertiary amine base such as triethylamine, tetramethylguanadine, diisopropylethyl amine and trimethylamine. The preferred tertiary amine is triethylamine. Alternatively, the salt of the sulfide compound can be preformed by reacting the sulfide compound with an inorganic base such as sodium hydroxide or potassium hydroxide. The reaction of the polymer support with the mercaptan takes place in a polar solvent that will swell the polymer but not react with the mercaptan such as tetrahydrofuran, N,N-dimethylformamide, benzene or toluene. The preferred solvent is tetrahydrofuran.

The sulfide resin is oxidized to a sulfoxide resin of the formula

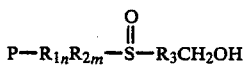

where P, $R_1$, $R_2$, $R_3$, n and m are defined above. The oxidation can be effected by any of the methods known in the art of oxidation such as hydrogen peroxide, peracids, iodobenzene dichloride, sodium periodate, etc. The preferred method of oxidation is with m-chloroperbenzoic acid in methylene chloride at 0 to 25° C.

The following examples are for illustration purposes only and are not intended to limit the scope of this invention.

EXAMPLE 1

A crosslinked polystyrene support was functionalized as follows:

In a 500 ml round-bottom flask were placed 20.00 g of a chloromethylated 1% cross-linked polystyrene; (Merrifield resin) 200–400 mesh, 1.1 meq chloride/gram, 22 mmol; 160 ml of dry tetrahydrofuran (THF); 6.32 g (45 mmol) of 4-mercaptobenzyl alcohol and 6.6 ml (4.8 g, 48 mmol) of triethylamine. The flask was placed on a rotary evaporator equipped with a condenser which allowed reflux of solvent into the flask, placed under a nitrogen atmosphere and immersed in a water bath at 60° C. The flask was rotated for 24 hours. After cooling to room temperature, the resin was transferred to a shaker vessel equipped with a coarse glass frit for filtering and washed successively three times with 160 ml each of THF, 20% water/80% THF (v:v), 50% water/50% methanol and methanol. The resin was dried under vacuum. The resin was submitted for elemental analysis and found to contain 0.44 weight percent chloride (0.12 meq/g) and 2.43 weight percent sulfur (0.79 meq/gram). Infrared analysis of this resin showed only a trace of the band at 1265 cm$^{-1}$ due to the chloromethyl group indicating almost complete reaction of the chloromethyl with the mercaptan.

The functionalized resin was oxidized from a sulfide to a sulfoxide as follows:

In a 500 ml round-bottom flask were placed 17.1 g (0.79 meq sulfur/g, 13.5 mmol) of the above functionalized resin and 170 ml methylene chloride. After cooling to 5° C., 2.47 g of 83.3% meta-chloroperbenzoic acid oxidizing agent (2.06 g active peracid, 11.9 mmol) was slowly added over a fifteen minute period. After the addition, the flask was rotated on a rotary evaporator in a cold room at 7° C. for 24 hours. The resin was transferred to a shaker vessel and washed successively three times each with 150 ml of methylene chloride and methanol.

Infrared analysis of this group showed a strong band at 1020 cm$^{-1}$ due to the sulfoxide group.

Synthesis 1

Anchoring the First Amino Acid

The amino acid was anchored to sulfoxide resin as follows:

In a shaker vessel was placed 4.00 g (0.79 meq sulfur/g, 3.16 mmol) of sulfoxide resin and 40 ml methylene chloride. The following reagents were added, in order, with a 1 minute shake between additions; 2.10 g (7.9 mmol) of N-(tert-butyloxycarbonyl)-L-phenylalanine, 40 mg (0.33 mmol) of N,N-dimethyl-4-aminopyridine and 1.5 ml (1.37 g, 10.9 mmol) of 1,3-diisopropylcarbodimide. The reaction mixture was shaken at room temperature for 24 hours, the solvent drained and the resin washed successively three times each with 40 ml methylene chloride, methanol and methylene chloride. To the wet resin was added 40 ml methylene chloride, 3.2 ml (2.43 g, 18.8 mmol) N,N-diisopropylethylamine and 1.5 ml (1.80 g, 17.7 mmol) acetic anhydride, and the vessel was shaken for 2 hours. After draining the solvent, the resin was washed three times with 40 ml methylene chloride and methanol, and dried under vacuum. Amino acid analysis of this resin showed a phenylalanine loading of 0.64 meq/g at resin.

Deprotecting the Sulfoxide Resin and Capping the Residual Sulfide Resin

The resin was deprotected and residual sulfide resin was capped as follows:

In order to remove any phenylalanine attached to a sulfide linker group and at the same time cap these groups, the above resin was treated with 40 ml of 45% trifluoroacetic acid/5% anisole/50% methylene chloride (v:v:v) for 21 hours, washed three times with 40 ml each of methylene chloride and methanol, and dried under vacuum. Amino acid analysis of this resin showed a phenylalanine loading of 0.58 meq/g of resin. This resin has only phenylalanine attached to a sulfoxide linker group, (the sulfide linker groups have been blocked) and is now ready for use in peptide synthesis.

Reducing the Sulfoxide Linkage and Cleavage

The resin linkage reduced to a sulfide linkage and the amino acid was cleaved from the resin under low HF conditions as follows:

A sample of the above phenylalanine-substituted sulfoxide resin (0.50 g, 0.58 meq/g, 0.29 mmol) was treated with a mixture of 1.0 ml p-cresol, 6.5 ml dimethyl sulfide and 2.5 ml anhydrous hydrogen fluoride for 2 hours at 0° C. After stripping the reagents under vacuum, the resin was successively washed twice with 5 ml each of methylene chloride, trifluoroacetic acid, methylene chloride and methanol and then dried under vacuum. Amino acid analysis of the resin showed a phenylalanine content of 0.062 meq/g, indicating that an 89% cleavage yield had occurred. Infrared analysis showed no sulfoxide band at 1020 cm$^{-1}$, indicating that the sulfoxide group had been fully reduced.

In an alternative method of reducing the sulfoxide linkage and cleaving the amino acid from the resin, low trifluoromethanesulfonic acid conditions were used as follows:

A sample of phenylalanine-substituted sulfoxide resin from above (0.20 g, 0.58 meq/g, 0.12 mmol) was treated with a mixture of 0.60 ml dimethyl sulfide, 1.2 ml trifluoroacetic acid and 0.20 ml trifluoromethanesulfonic acid at room temperature for 1 hour. The resin was washed three times successively with 5 ml each of trifluoroacetic acid, methylene chloride and methanol, then dried under vacuum. Amino acid analysis of the resin showed a phenylalanine content of 0.055 meq/g, indicating that a 91% cleavage yield had occurred. Infrared analysis for the presence of the sulfoxide group was complicated by bands which were attributed to trifluoromethanesulfonic acid.

Synthesis II

A dipeptide of L-leucine and L-phenylalanine was prepared using the above described resin. N-(tert-butyloxycarbonyl)-L-leucine was coupled using the procedure of Synthesis 1. Amino acid analysis of this resin showed a leucine content of 0.75 meq/g. When treated with 45% trifluoroacetic acid to deprotect and cap the residual sulfide resin as in Synthesis 1, the leucine content dropped to 0.49 meq/g. A sample of this resin (0.994 g, 0.49 mmol) was washed twice with a solution of 10% diisopropylethylamine in methylene chloride, followed by three washes with methylene chloride to neutralize the resin. The resin was coupled with N-(tert-butyloxycarbonyl)-L-phenylalanine by suspending the resin in 10 ml methylene chloride and adding 464 mg (1.75 mmol) N-(tert-butyloxycarbonyl)L-phenylalanine and then 0.27 ml (235 mg, 1.86 mmol) N,N-diisopropylcarbodiimide. After shaking for two hours, the resin was washed three times with methylene chloride and dried under vacuum. Amino acid analysis showed the leucine content to be 0.40 meq/g and the phenylalanine content to be 0.40 meq/g.

The sulfoxide resin was deprotected and the linkage reduced by anhydrous hydrogen chloride and the peptide was cleaved from the resin by trifluoroacetic acid as follows:

A sample of the above coupled resin from Example 2 (100 mg, 0.04 mmol) was shaken for four hours with 5 ml of a 4.1 molar solution of anhydrous hydrogen chloride in dioxane. The resin was washed five times with 5 ml methylene chloride and dried under vacuum. Amino acid analysis showed the following amino acid content: leucine (0.28 meq/g) and phenylalanine (0.32 meg/g), indicating that a 25% cleavage had occurred. The resin was then treated with 5 ml of 45% trifluoroacetic acid/5% anisole/50% methylene chloride (v:v:v) for twenty-four hours, filtered, washed six times with 5 ml methylene chloride and dried under vacuum. Amino acid analysis of this resin showed the following amino acid content: leucine (0.08 meq/g) and phenylalanine (0.11 meq/g), indicating a 72-81% cleavage had occurred. In a separate experiment, when the treatment with anhydrous hydrogen chloride was extended to twenty-four hours and the trifluoroacetic acid treatment maintained at twenty-four hours, no change in the amount of cleavage was observed.

We claim:

1. A method of synthesizing a resin for solid phase peptide synthesis comprising
    (1) reacting a polymer support, P, capable of undergoing a nucleophilic reaction with a mercaptan of the formula $HS-R_3CH_2OH$ where $R_3$ is a substituted or unsubstituted phenylene to form a sulfide resin of the formula

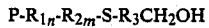

where $R_1$ is a substituted or unsubstituted aromatic wherein the substitutents of $R_3$ and $R_1$ are selected from the group consisiting of hydrogen, methyl, ethyl, phenyl, nitro and halogens, and $R_2$ is an alkylene having 1 to 20 carbon atoms and n and m independently equal 1 to 0 and
    (2) oxidizing the sulfide resin to form a sulfoxide resin of the formula

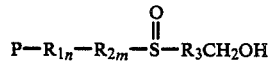

where $R_1$, $R_2$, $R_3$, n and m are defined above.
2. The method of claim 1 wherein the polymer support is a crosslinked polystyrene gel.
3. The method of claim 1 where n and m equal 1, $R_1$ and $R_3$ are unsubstituted phenyls and $R_2$ is methylene.
4. The method of claim 1 wherein the sulfoxide resin is of the formula

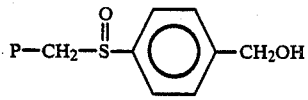

* * * * *

UNITED STATES PATENT AND TRADEMARK OFFICE
CERTIFICATE OF CORRECTION

PATENT NO. : 4,801,665

DATED : January 31, 1989

INVENTOR(S) : Daniel P. Getman et al

It is certified that error appears in the above-identified patent and that said Letters Patent is hereby corrected as shown below:

Col. 1, line 55, delete "eptide" and substitute therefor --peptide--.

Col. 2, line 2, delete "p-alkoxybenzyl" and substitute therefor --p-alkoxybenzyl--; line 4, delete "Id." and substitute therefor --Id.--; line 17, delete "p-Methylsulfinylbenzyl" and substitute therefor --p-methylsulfinylbenzyl--; line 20, delete "p-methylsulfinylbenzyl" and substitute therefor --p-methylsulfinylbenzyl--.

Col. 3, line 42, delete "m-divinyl" and substitute therefor --m-divinyl--.

Col. 4, line 25, delete "p-(mercapto)" and substitute therefor --p-(mercapto)--; line 26, delete "o-(mercapto)benzyl" and substitute therefor --o-(mercapto)benzyl--; line 26, delete "p-(mercap-" and substitute therefor --p-(mercap- --; line 27, delete "o-chloro-" and substitute therefor --o-chloro- --;

line 54, delete "m-chloroper-" and substitute therefor --m-chloroper- --.

UNITED STATES PATENT AND TRADEMARK OFFICE
CERTIFICATE OF CORRECTION

PATENT NO. : 4,801,665

DATED : January 31, 1989

INVENTOR(S) : Daniel P. Getman et al.

It is certified that error appears in the above-identified patent and that said Letters Patent is hereby corrected as shown below:

Col. 8, line 30, add --where P is a crosslinked polystyrene resin--.

Signed and Sealed this

Sixth Day of October, 1992

*Attest:*

DOUGLAS B. COMER

*Attesting Officer*     *Acting Commissioner of Patents and Trademarks*